United States Patent
Stewart et al.

(10) Patent No.: US 7,201,754 B2
(45) Date of Patent: Apr. 10, 2007

(54) DEVICE FOR INSTALLING AN ANCHOR IN A BONE

(76) Inventors: Kenneth Stewart, 6938 Stetson Street Cir., Sarasota, FL (US) 34243; Thomas M. Sweeney, II, 4717 Elder Berry Dr., Sarasota, FL (US) 34241

( * ) Notice: Subject to any disclaimer, the term of this patent is extended or adjusted under 35 U.S.C. 154(b) by 292 days.

(21) Appl. No.: 10/359,448

(22) Filed: Feb. 6, 2003

(65) Prior Publication Data

US 2003/0153921 A1 Aug. 14, 2003

Related U.S. Application Data

(60) Provisional application No. 60/355,215, filed on Feb. 8, 2002.

(51) Int. Cl.
*A61B 17/58* (2006.01)
(52) U.S. Cl. .......................... 606/72; 606/73
(58) Field of Classification Search ................. 606/72, 606/73
See application file for complete search history.

(56) References Cited

U.S. PATENT DOCUMENTS 6,136,032 A * 10/2000 Viladot Perice et al. . 623/21.18
2001/0053913 A1* 12/2001 Freedland ..................... 606/73

\* cited by examiner

*Primary Examiner*—Tom Barrett
*Assistant Examiner*—David A. Izquierdo
(74) *Attorney, Agent, or Firm*—Evelyn M. Sommer

(57) ABSTRACT

A device and method for installing an anchor in a bone of a patient which employs an anchor body having expandable side walls in a tapered shape with retention members on their external surfaces, and an expansion member within the anchor body which is pulled to an engaged position. While in the engaged position the expansion member presses on the inside of the side walls to expand them outwardly to engage the retention members with the bone walls. The side walls have containment ring sections at their distal ends for retaining the expansion member inside the anchor body. The expansion member may be formed as a conical plug with a central aperture and tab recesses on its underside for insertion of an elongated scissors-type instrument with movable prongs that engage into the tab recesses of the expansion plug.

18 Claims, 11 Drawing Sheets

FIG. 8A
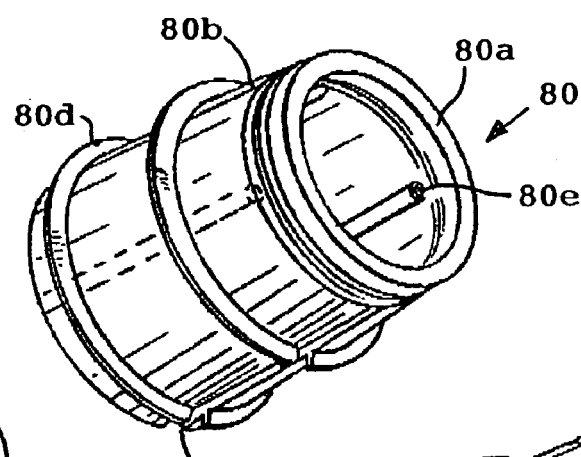
FIG. 8B
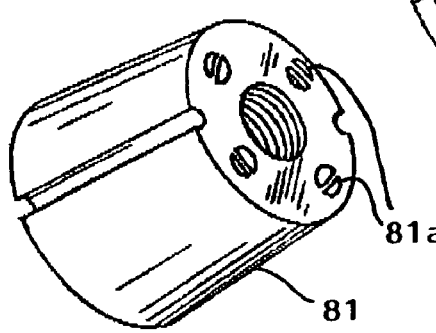
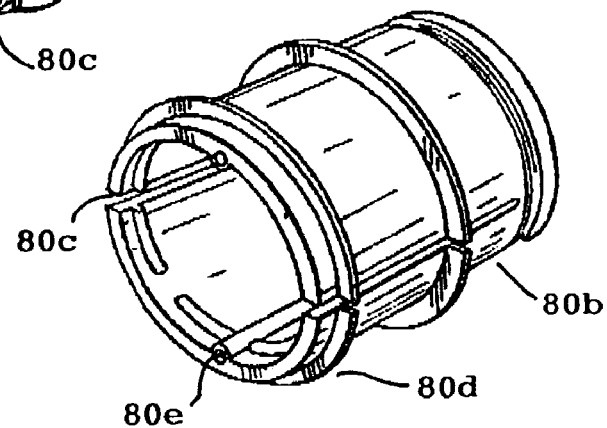
FIG. 8C

DEVICE FOR INSTALLING AN ANCHOR IN A BONE

This U.S. patent application claims the priority of U.S. Provisional Application No. 60/355,215 filed on Feb. 8, 2002.

TECHNICAL FIELD

This invention generally relates to surgically installing an anchor in a bone of a patient, and more particularly, to an improved device that allows for quick and easy installation of an anchor in the bone.

BACKGROUND OF INVENTION

Suture anchors are used to secure sutures to bones during joint reconstructive surgery or arthroscopic surgical procedures. The anchor allows a suture to be secured to it, whereas it would otherwise be difficult to secure the suture to the bone material. For example, suture anchors are used to connect ligaments or tendons to bones during knee, shoulder or elbow reconstruction or repair operations. A bone anchor must be easy to install and must remain firmly in place for the intended time. It must be able to resist withdrawal forces exerted by the attached suture, and must also be physically compatible with the bone structure and other body tissues.

U.S. Pat. No. 4,738,255 disclosed a suture anchor having a collar with a slotted end that expands when a plug or ram is pulled into the distal end of the collar. The ram is pulled into the slotted collar by tension exerted on a line that runs axially through a mandrel from which the collar is suspended.

U.S. Pat. No. 4,013,071 disclosed an orthopedic screw having an expandable tip that enhances bone retention. The expandable tip includes side slits that extend through the distal end of the screw and are flared by advancing a rod-shaped expansion member through an internal bore of the orthopedic screw. When the rod shaped expansion member is withdrawn, the tip returns to its original (unexpanded) shape.

U.S. Pat. No. 5,236,445 showed a bone anchor that has an open proximal end and a body that tapers to a solid distal tip. The anchor is placed deep in a borehole in a bone using an insertion instrument with a spherical knob that snaps into a corresponding recess in the anchor. Once the anchor is in place, the anchor is expanded by rotating the oval-shaped instrument to bear against the walls of the anchor and expand them outwardly to press their external ridges or fins against the walls of the borehole to prevent retraction.

U.S. Pat. No. 5,957,953 disclosed a suture anchor having an expandable outer member and an inner member that is progressively threaded or ratcheted into the outer member in order to cause a plurality of slotted arms to expand radially outward to hold the anchor in place in the bone.

U.S. Pat. No. 6,136,032 showed a frustoconical anchor body formed with side expansion slits. An expansion cone is threaded into the proximally-facing opening in the anchor body in order to expand its external walls and press its external fins against the bone wall to oppose withdrawal of the device after it has been implanted.

The prior devices have the problem that threading or advancing an expansion cone or ram into a proximally-facing opening of the anchor body has the effect of pushing the anchor body deeper into the borehole in the bone where it is more difficult to connect in a predictable way with the suture. It is thus difficult to positively locate the anchor in a desired position with its proximal end aligned with the bone surface.

SUMMARY OF INVENTION

In accordance with the present invention, an anchor device for installation in a borehole formed in a bone of a patient comprises:

(a) an anchor body to be inserted in a borehole formed in a surface of a bone having expandable side walls in a tapered shape with a narrower proximal end thereof to face outwardly from the borehole and a wider distal end thereof to be inserted into the interior of the borehole, wherein said side walls have retention members formed on their external surfaces for inhibiting the anchor body from being retracted from the borehole when the side walls are expanded;

(b) an expansion member positioned in an interior space defined within the side walls of the anchor body and movable from a disengaged position toward the distal end of the anchor body to an engaged position toward the proximal end of the anchor body, wherein when said expansion member is moved to the engaged position, it presses on the inside of the side walls of the anchor body to expand them outwardly in order to thereby engage the retention members with the borehole walls to inhibit retraction from the bone, and wherein said proximal end of the anchor body has a central aperture to allow insertion of a distal end of an elongated expansion tool into the interior space of the anchor body in order to grasp the expansion body in its disengaged position in the anchor body and pull the expansion member to the engaged position to thereby expand the side walls of the anchor body outwardly.

In preferred embodiments of the invention, the anchor body has slightly tapered walls that are sectioned by slits to form expandable side wall sections below an expansion joint or deformation wrinkle. The expansion member is formed as a frustoconically shaped plug. The inside surfaces of the side walls have containment ring sections formed at their distal ends for retaining the expansion member inside the anchor body. The expansion tool may be an elongated scissors-type instrument that has a pair of movable prongs that can be scissored together to allow insertion of the tool into the aperture in the proximate end of the anchor body, and extended to engage into tab recesses formed in the underside of the expansion member. In another embodiment, the expansion tool can have a threaded tip for threading into and out of engagement with a threaded bore formed in the expansion member.

The inside of the anchor body may be provided with guide ribs that fit in corresponding slot recesses formed in the sides of the expansion member for guiding its movement from the disengaged to the engaged position. The guide ribs may be formed as hollow tubes to allow insertion and squeezing together of the straight ends of a removal tool to dislodge the expansion member from the engaged position in the event removal of the anchor is desired. The retention members may be formed as annular cutter blades that cut into the walls of the bone when the side walls of the anchor body are expanded. The anchor body may also have an anchor plate or collar at its proximal end to positively locate the anchor body in a desired position with its proximal end aligned and bonded with the bone surface.

Other objects, features, and advantages of the present invention will be explained in further detail in the following detailed description of preferred embodiments of the invention, having reference to the appended drawings.

BRIEF DESCRIPTION OF DRAWINGS

FIG. 8A is a top view in perspective showing another embodiment of an anchor device, FIG. 8B shows a plug for use with the anchor device having sleeves or anchor points on its upper surface for attachment of sutures thereto, and FIG. 8C shows a bottom view in perspective.

DETAILED DESCRIPTION OF INVENTION

Figure 1:
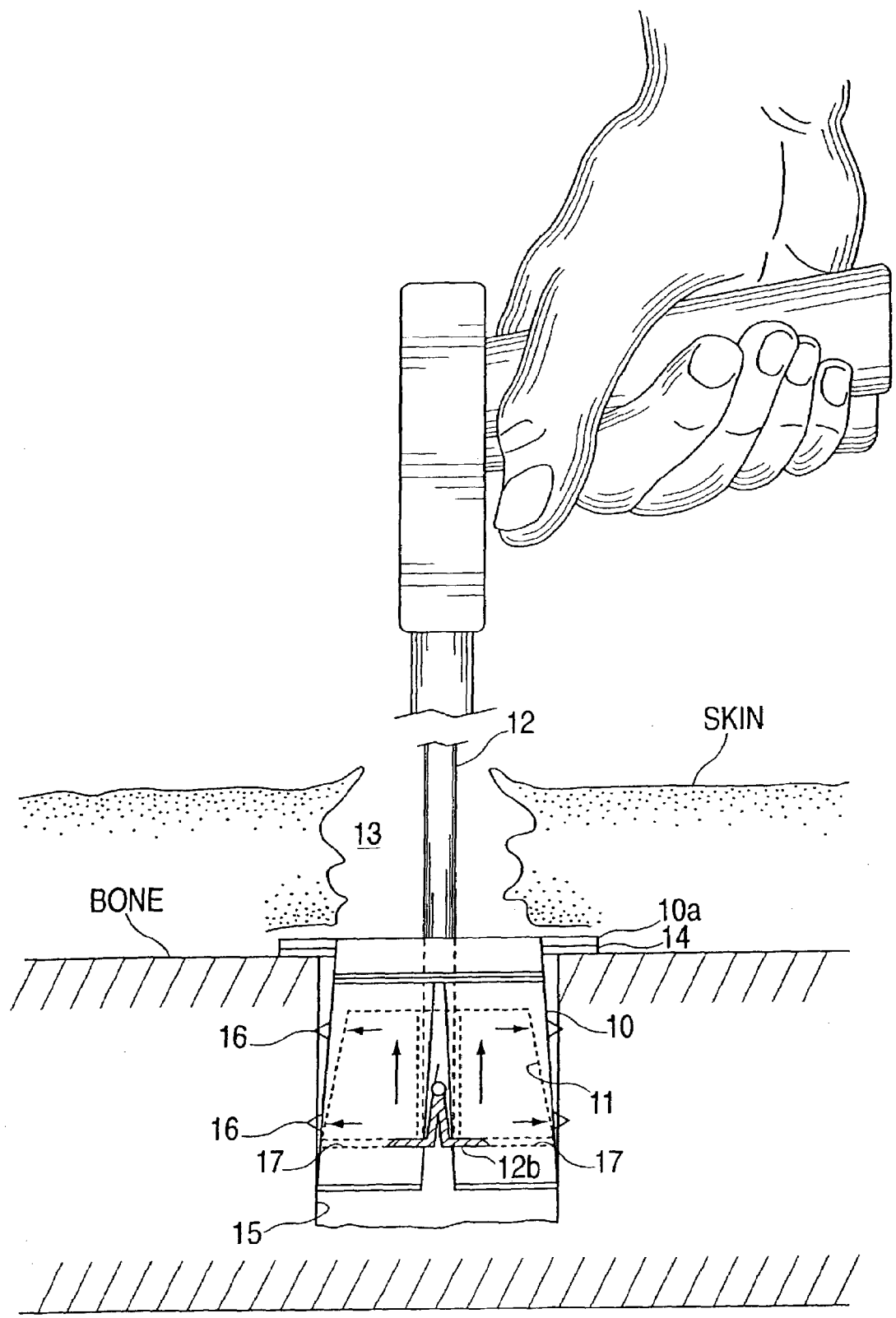
FIG. 1 illustrates an anchor device in accordance with the present invention and the manner of installing the device in a bone of a patient.

Referring to FIG. 1, a device for surgically installing an anchor in bone includes an anchor body 10, an expansion member 11, and an installation tool 12. The anchor body 10 is installed in a patient's bone as a terminal for fixation of fractures or joints or to repair or attach tendons or ligaments to the bone. An incision 13 is first made through the patient's skin (SKIN) or tissue to expose the work area of the bone (BONE). A borehole 15 is drilled into the bone for installation of the anchor body 10 therein. The anchor body 10 has expandable side walls with a tapered shape, with a narrower proximal end thereof(toward the top of the figure) to face outwardly from the borehole in the bone and a wider distal end thereof (toward the bottom of the figure) to be inserted in the borehole. The anchor body 10 may have an upper anchor plate 10a that overlies or is adhered with an adhesive layer 14 over the borehole in order to positively locate the anchor unit aligned with the surface of the bone. The expansion member 11 has a tapered shape and is positioned in the interior space within the side walls of the anchor body 10. It is used to expand the side walls of the anchor body outwardly in order to engage retention members 16 with the borehole walls to inhibit retraction from the bone (to be explained in further detail below).

The expansion tool 12 has a handle with a trigger for operation and a long stem or probe with a distal end for insertion through an aperture in the proximal end of the anchor body 10 to grasp or engage the expansion member 11. In the embodiment shown, the tool 12 is of the scissors-type with a pair of movable prongs or tabs 12b that can be scissored to fold together in overlapped fashion (when the trigger of the tool is pulled) to allow the probe end to be inserted through the aperture in the anchor body, and released to extend outwardly (when the trigger of the tool is released) to engage in tab recesses 17 formed on the underside of the expansion member. The expansion tool 12 is used to pull the expansion member 11 from the disengaged position toward the distal end of the anchor body to the engaged position toward the proximal end of the anchor body (in the direction of the vertically pointing arrows), in order to expand the side walls (in the direction of the laterally pointing arrows) for pressing retention members 16 against the borehole walls.

The expansion tool can be formed as a surgical, stainless steel instrument, approximately 8 to 10 inches long, with a pistol grip handle and trigger that will allow gripping of all four fingers against the thumb and thenar eminence to apply significant pressure. As an alternative to the scissors-type with movable tab ends, the tool can have a long thin stem with a threaded tip that engages with a threaded bore formed in the expansion member. The trigger can be used to activate a small battery-powered rotary drive motor for rotating the stem to thread the tip into the threaded bore to engage the expansion member, and reversed to thread the tip out of the bore to release the tool from the expansion member.

Figure 2:
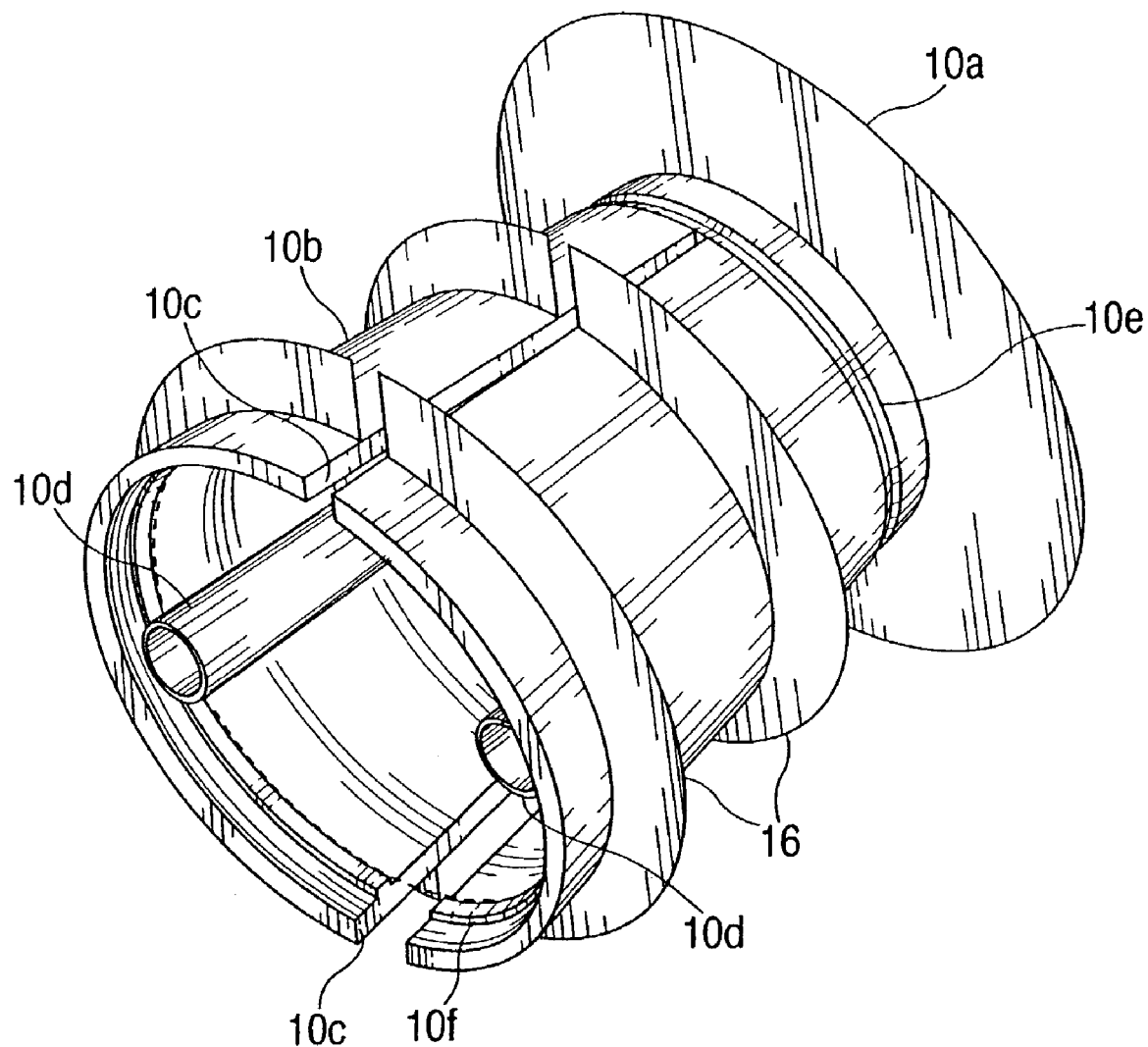
FIG. 2 is a perspective diagram showing an anchor body with tapered side walls, upper anchor plate, external deformation wrinkle, and conical expansion member inside thereof

Referring to FIG. 2, a preferred embodiment of the anchor device 10 is shown with an anchor body formed with a top anchor plate 10a at its proximal end, tapered side walls 10b split in half sections by slits 10c, and containment ring sections 10f on the inside of the side wall sections at their distal ends for holding the expansion member 11 inside the anchor body. The proximal end has a central opening to allow the expansion tool access to the expansion member. The anchor body and the expansion member are both tapered to allow the latter to move inside the other and to press against the side walls at the engaged position to expand them outwardly. The side walls of the anchor body may have only a slight taper (almost cylindrical) so that only a small movement of the expansion member upwards is needed to exert the requisite force on the side walls. The side wall sections have two rings of arcuate cutter blades as the retention members 16 formed on their external surfaces for engaging with the borehole walls of the bone. The side walls sections merge together into a solid ring above an expansion joint 10e. The latter provides a flexible joint between the unitary part of the side walls and their lower parts which are split into expandable sections. A pair of hollow ribs 10d may be provided on the inside surfaces of the side wall sections 10b for guiding the movement of the expansion member 11 between disengaged and engaged positions inside the anchor body.

The expansion member 11 and retention members 16 hold the anchor body in place after expansion of the side walls. Above the top edge of the expansion joint, a "blister ring" might be provided on the inside surfaces of the side wall to further act as a detent with a corresponding blister ring on the top edge of the expansion member to lock it in place with sufficient friction fit, although not strong enough friction to prevent future removal. As an alternative, a single blister ring may be provided on the inside surfaces of the side wall at a position just below the bottom wall of the conical plug 11 when it is in the engaged position. When the plug is raised, the bottom edge would be held in check by the blister ring to prevent downward migration of the plug.

Figure 3:
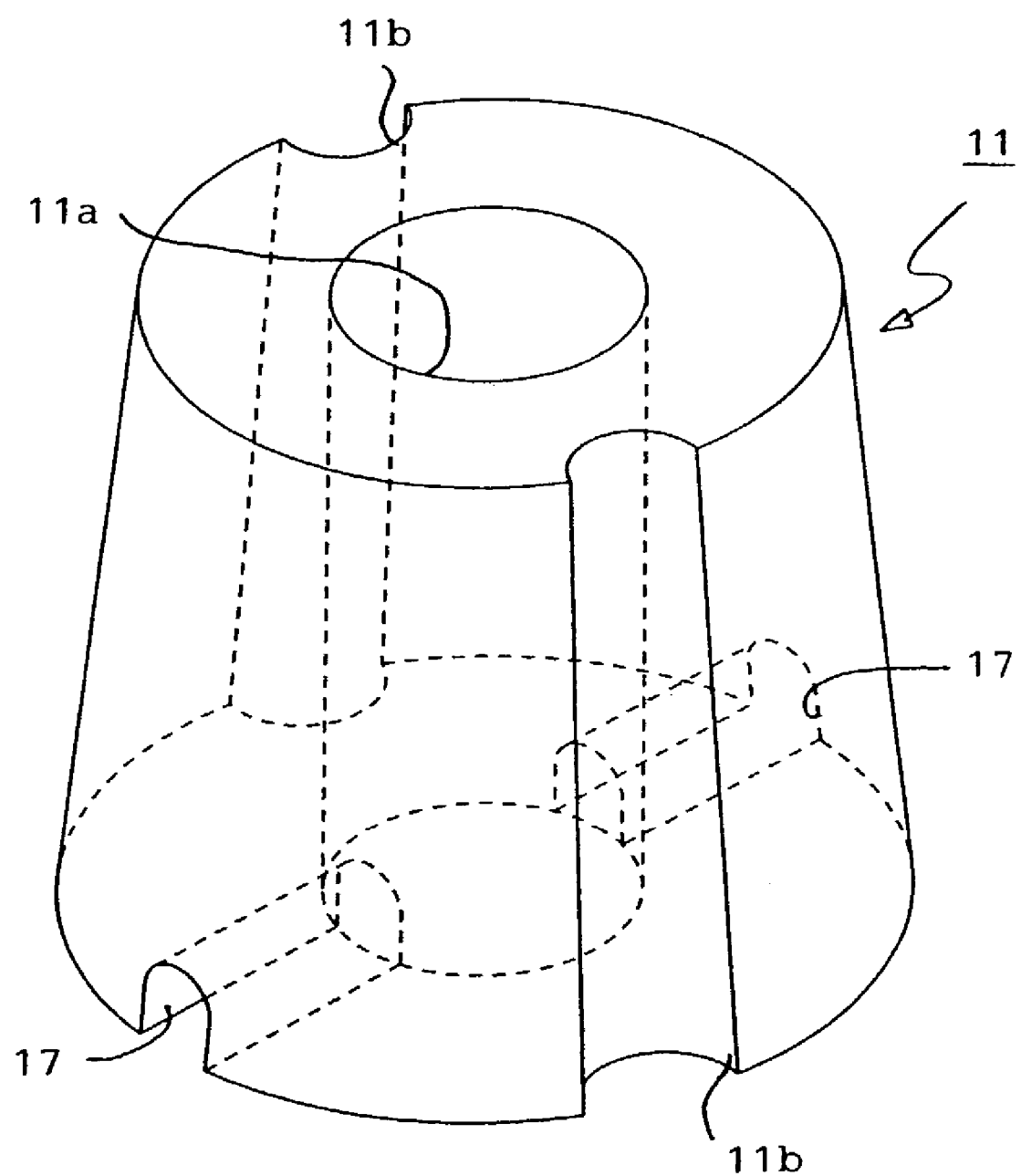
FIG. 3 is a diagram of one embodiment of the conical expansion member having recesses formed on the underside thereof for engagement with an expansion tool of the scissors-type.

In FIG. 3, a preferred embodiment of the expansion member 11 is shown in the form of a frustoconical plug which is made, for example, of a hard rubber or synthetic material. The plug 11 has a central aperture for insertion of the expansion tool 12 (with prongs 12b retracted) to the bottom of the plug, where the prongs are then extended into tab recesses 17 formed in the underside surface of the plug 11. In this manner, the plug 11 can be pulled into the engaged position in the anchor body. Slot recesses 11b are formed on opposite sides of the conical plug 11 for sliding along the guide ribs 10d provided on the inside surfaces of the anchor body. The guide ribs may be formed as hollow tubes into which two straight prongs of a removal tool can be inserted, one into each hollow tube, and squeezed together while pushing downwardly to dislodge the plug from the engaged position in the anchor body. The use of the removal tool in the guide slot recesses 11b also helps to disengage the retention members 16 from the bone, in order to allow removal of the anchor body from the bone. The central aperture in the conical plug also allows for the introduction of pulverized and/or pelletized bone fragments or allograft materials to speed healing and union therewith.

Figure 4:
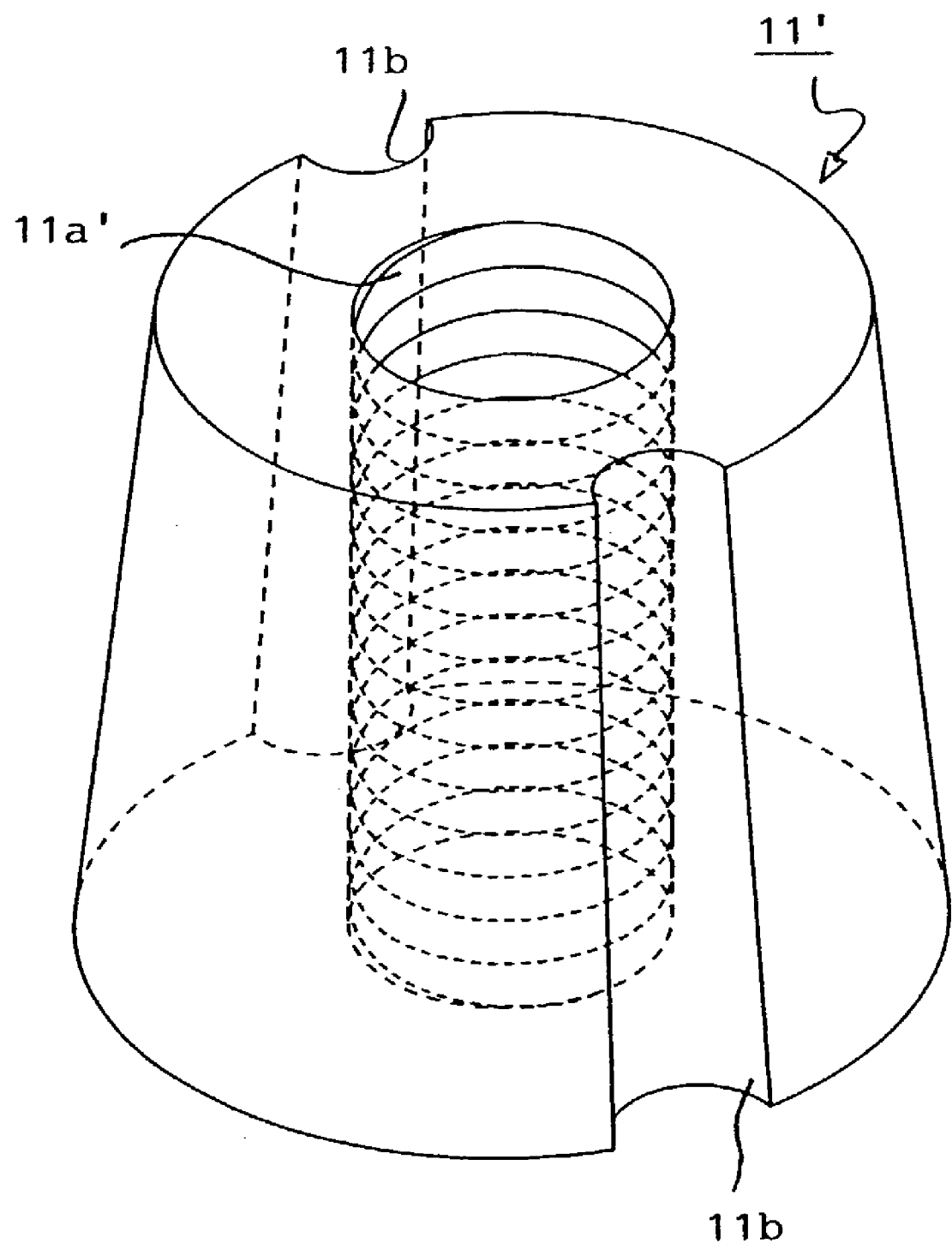
FIG. 4 is a diagram of another embodiment of the conical expansion member having a threaded bore for engagement with the threaded end of an expansion tool of the screw-type.

In FIG. 4, another embodiment of the expansion member 11' is shown in the form of a conical plug having a threaded bore 11a' for insertion of and engagement with the threaded tip of the expansion tool. Slot recesses 11b are used here as well for sliding along the guide ribs 10d on the inside surfaces of the anchor body.

Figure 5:
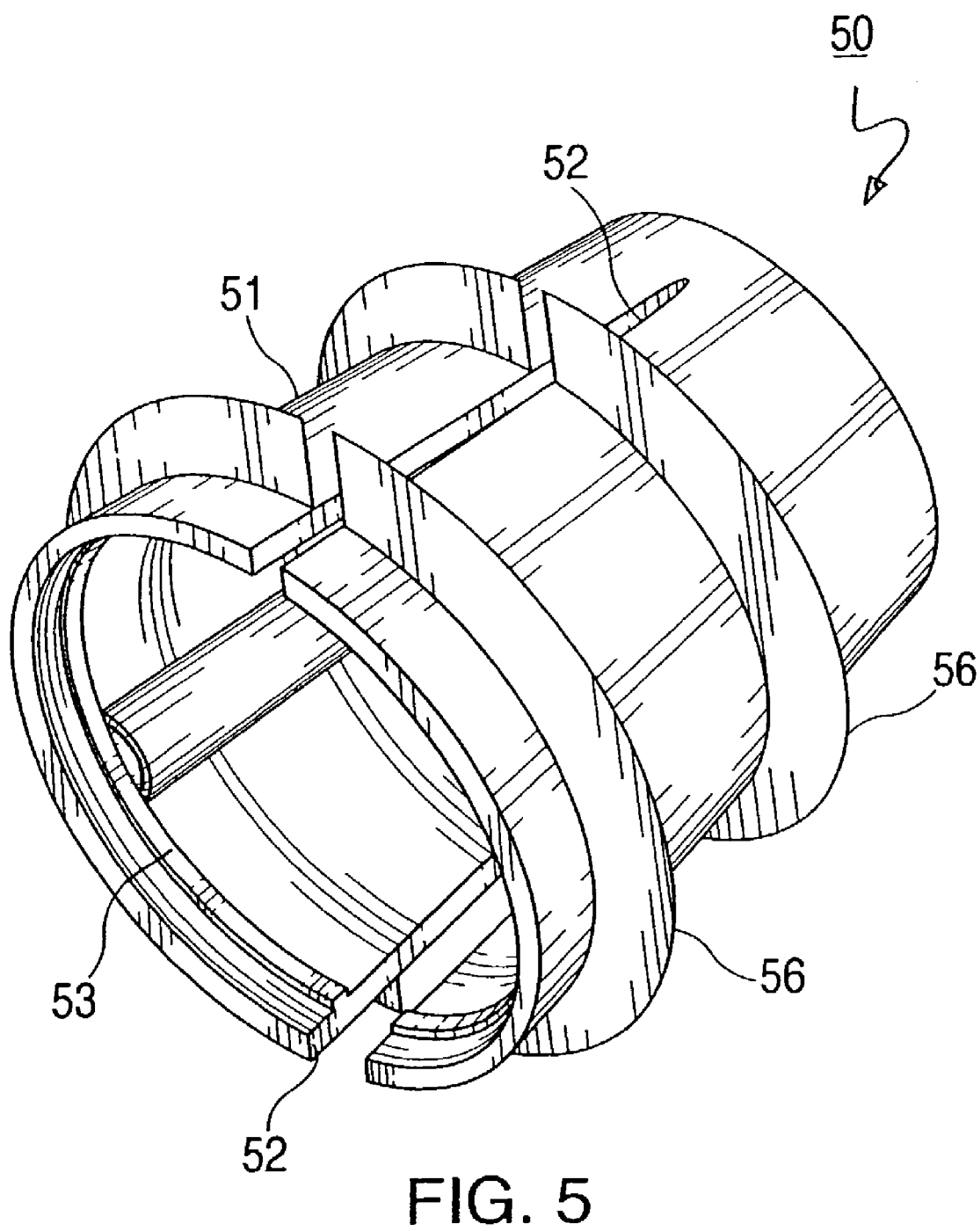
FIG. 5 is a perspective diagram showing another embodiment of the anchor body without the upper anchor plate and deformation wrinkle.

As shown in FIG. 5, a simpler form of an anchor body 50 has tapered side walls 51 joined as a solid ring at its upper part but divided by slits 52 to form sections (halves) at its lower parts. The containment ring 53 and arcuate cutter blade sections 56 are provided as before. An upper anchor plate is omitted. The anchor plate would be used primarily to form a strong bond to bone, but need not be used for other types of anchor deployments, such as for connecting tendons or ligaments. The expansion joint is also omitted, and instead the slits 52 are cut higher than the engaged position for the expansion member before to allow the side wall sections to move outwardly more flexibly.

Figure 6:
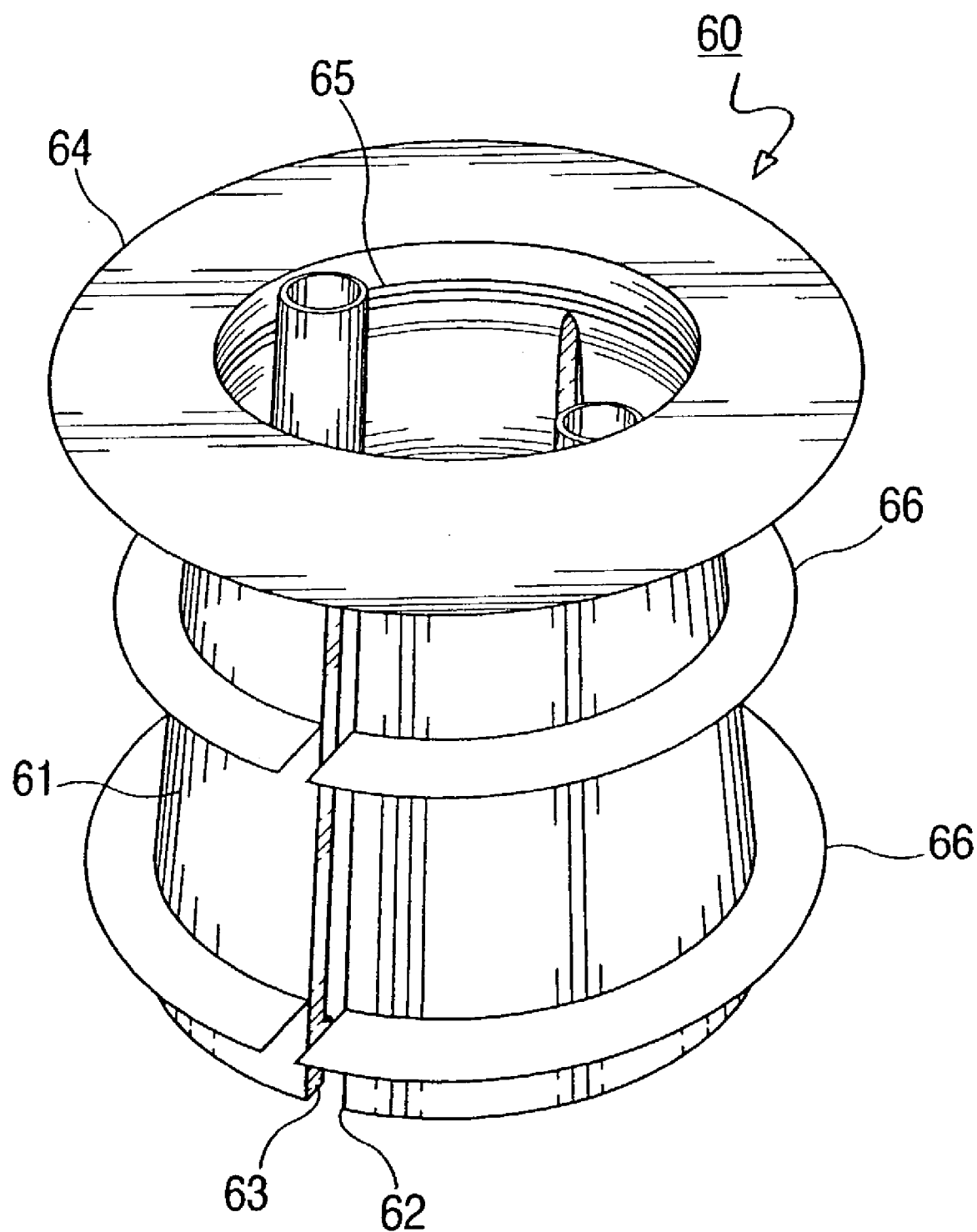
FIG. 6 is a perspective diagram showing a third embodiment of the anchor body with an upper anchor plate and an internal deformation wrinkle for the side walls on the inside thereof

In FIG. 6, a third embodiment of the anchor body 60 is provided with side walls 61 sectioned by slits 62, containment ring 63, an upper anchor plate 64, and cutter blades 66. Instead of an expansion joint, a deformation "wrinkle" (such as formed by scoring) 65 is formed on the inside surfaces of the side walls to provide some slight "play" for the side walls to be expanded outwardly. The deformation wrinkle could be eliminated, and the side walls may be expanded outwardly by using a "morse taper" or friction-fit expansion instead.

Figure 7B:
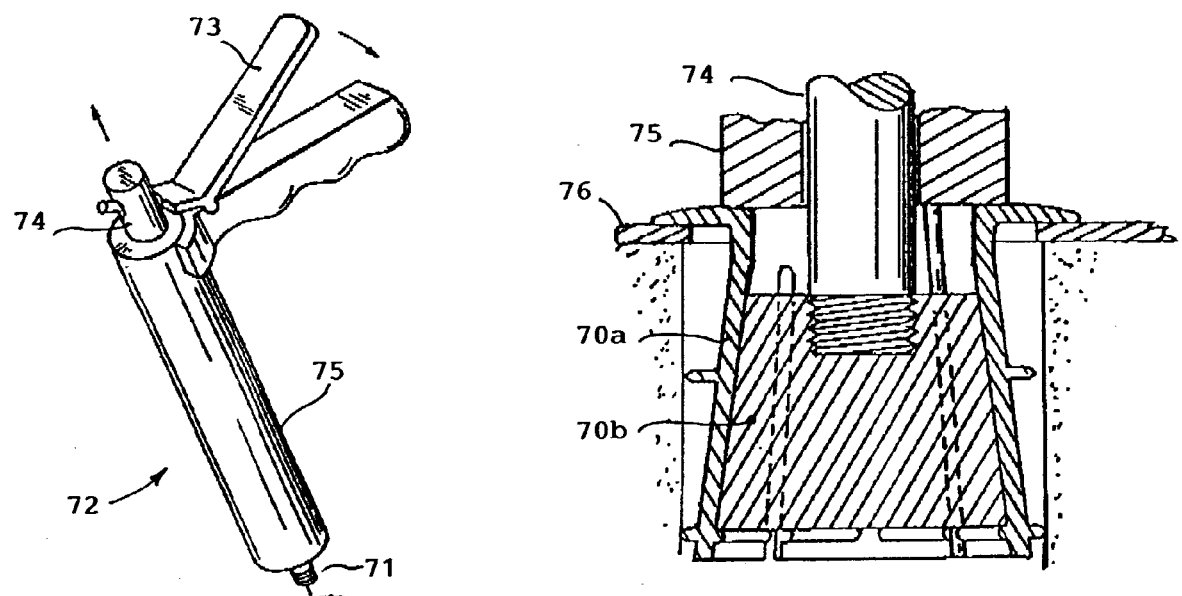
FIG. 7B shows a side view in section of the anchor device being installed.
Figure 7A:
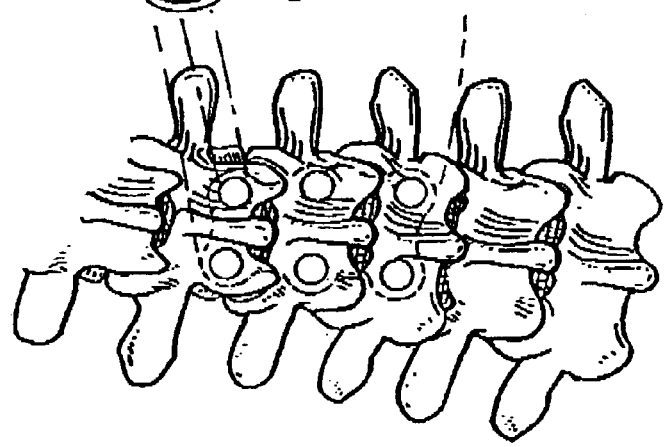
FIG. 7A illustrates another embodiment of an installation tool and its use to install an anchor device to anchor a brace to a section of cervical bones.
Figure 9B:
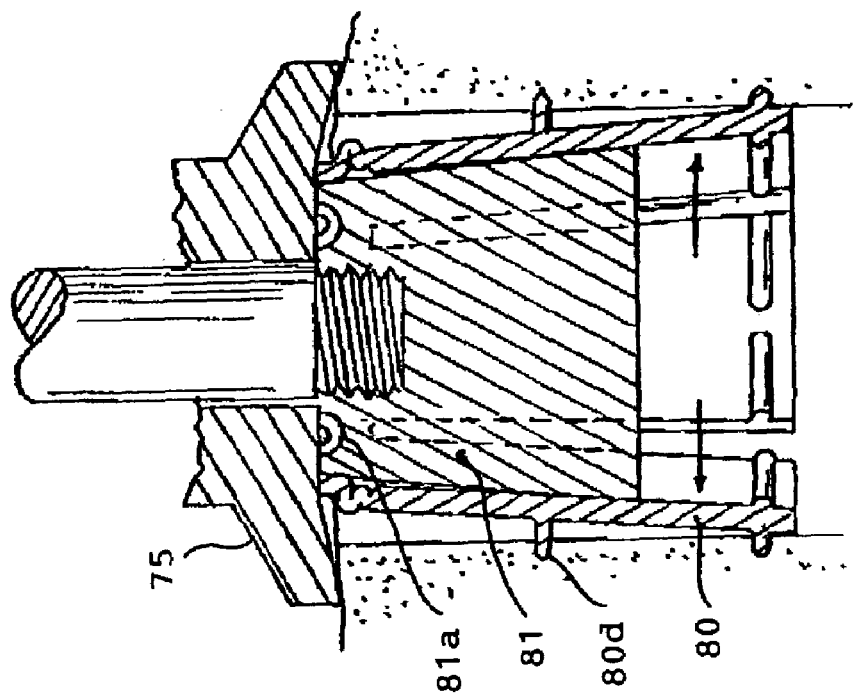
FIGS. 9A, 9B, 9C, and 9D are side views in section showing the installation of the anchor device in the bone cavity, the pulling up of the plug to anchor the device blades in the bone, removal of the installation tool, and then attachment of ligaments or tendons to the anchor device by threading sutures into the suture sleeves on the upper surface of the plug.
Figure 9A:
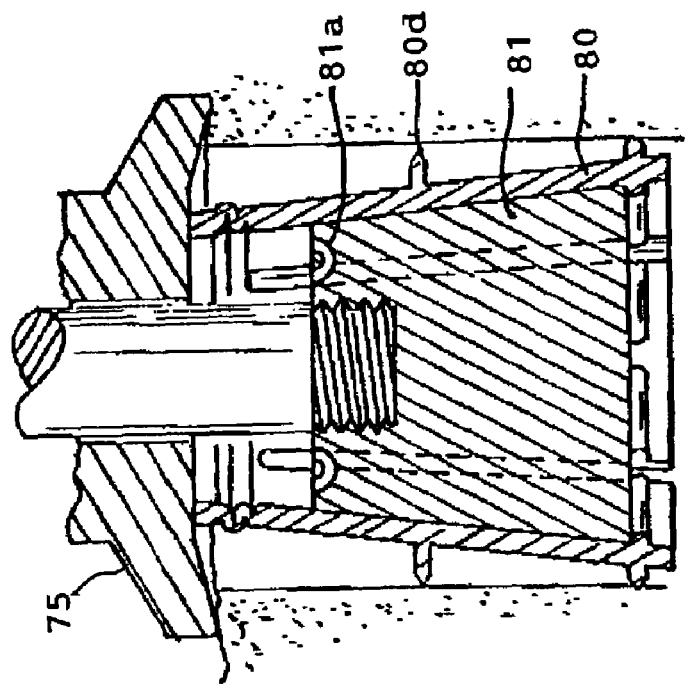
Figure 9C:
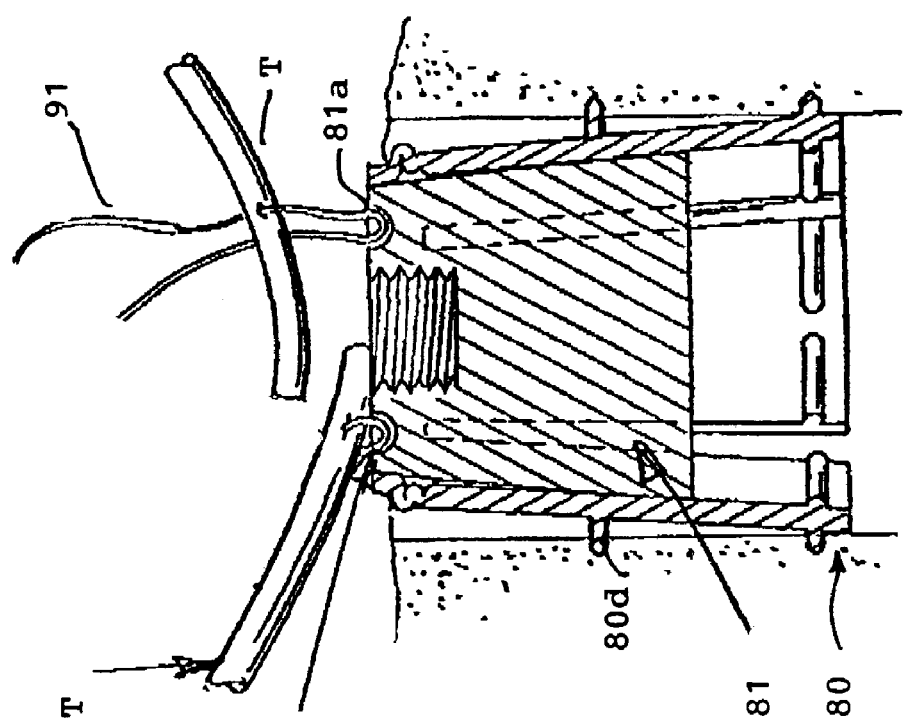
Figure 9D:
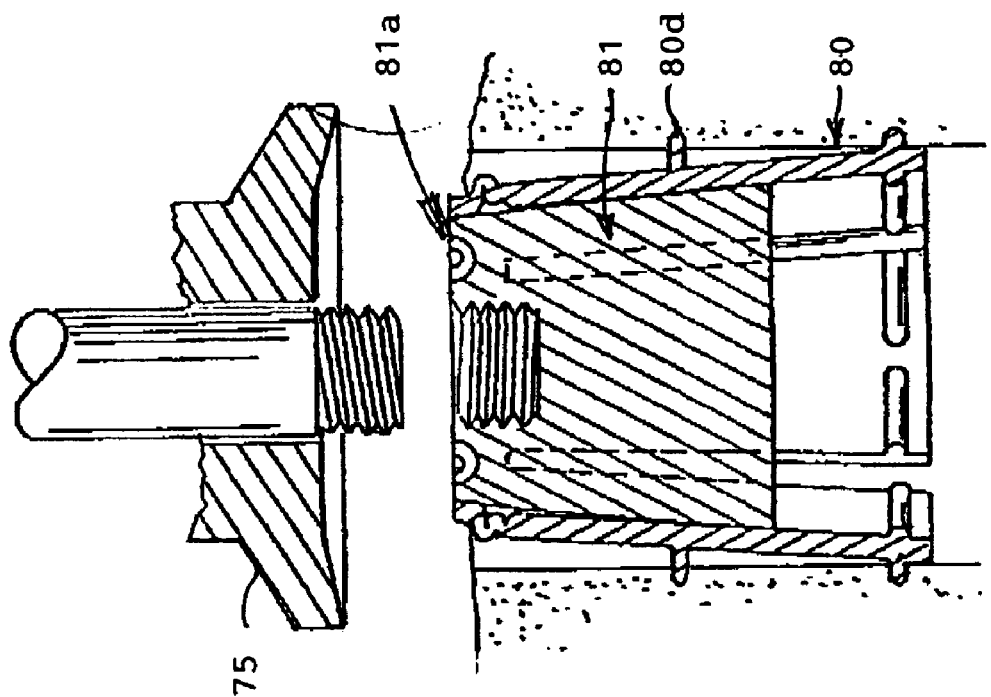

FIG. 7A illustrates another embodiment of an installation tool 72 and its use to install an anchor device 70a to anchor a brace 76 to a section of cervical bones. The tool 72 has a central rod 74 provided with a threaded end 71 which is threaded into a threaded hole in the plug 70b for the anchor device. Squeezing the handle 73 of the tool causes the central rod 74 to be displaced 10 outwardly relative to the barrel 75 of the tool (direction of the arrow at the top of the figure) to pull the plug 70b in the anchor device 70a upward so as to force the anchor blades into the bone, similar to the method described previously. The brace 76 has a spaced array of pairs of anchor holes 76a aligned with the cervical bones so that anchors can be installed in the anchor holes and respective ones of the cervical bones to brace the section of bones together. FIG. 7B shows a side view in section of the anchor device being installed. The bottom of the insertion tool barrel 75 serves to stabilize the proximal end of the anchor device 70a while the plug 70b is being engaged.

FIG. 8A is a top view in perspective showing another embodiment of an anchor device 80 having a top ring 80a defining a central aperture, side walls 80b, expansion slits 80c, blades 80d, and removal tubes 80e. FIG. 8B shows the plug 81 used with the anchor device 80 having sleeves 81a (or anchor points) on its upper surface for attachment of sutures thereto. Suture ends can be preloaded into the sleeves 81 for convenience, or attached during the surgical installation procedure. FIG. 8C shows a bottom view of the anchor device 80 in perspective.

FIGS. 9A, 9B, 9C, and 9D are side views in section showing the installation of the 25 anchor device 80 with the plug 81 having suture sleeves 81a into bone cavity, the pulling up of the plug 81 to anchor the device blades 80d in the bone, removal of the barrel 75 of the installation tool 72, and then attachment of ligaments or tendons T to the anchor device by threading sutures 91 into the suture sleeves 81a on the upper surface of the plug 80.

Figure 10B:
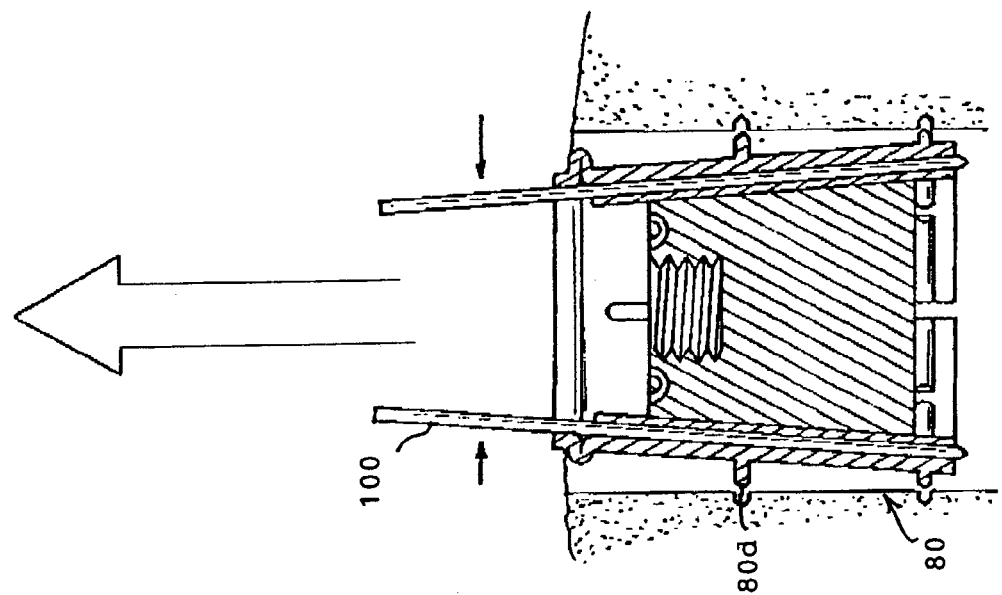
FIGS. 10A and 10B are side views in section illustrating removal of the anchor device from the bone.
Figure 10A:
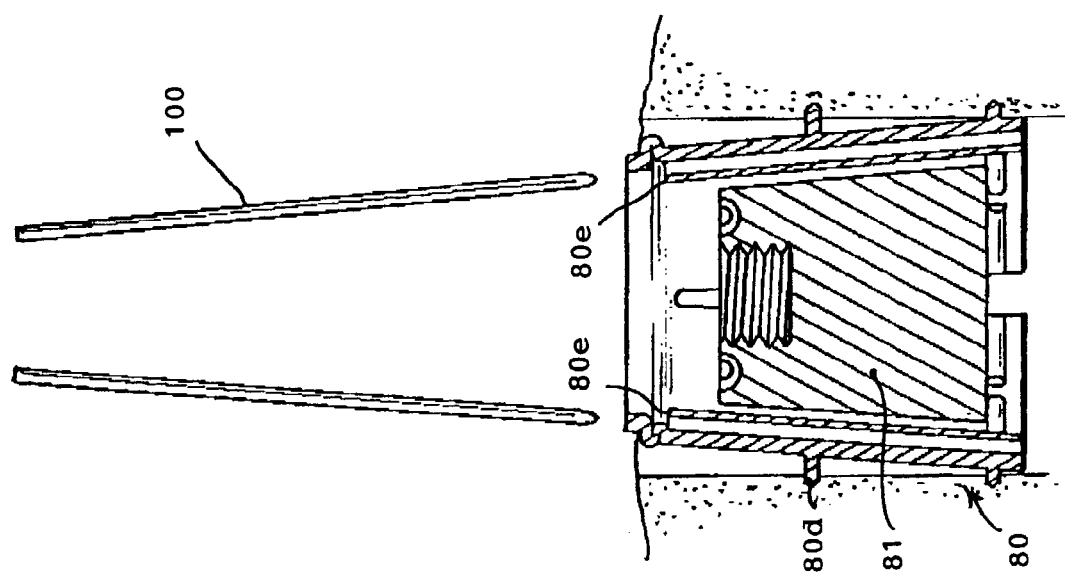

FIGS. 10A and 10B are side views of the anchor device 80 in section illustrating its removal from the bone. The removal procedure starts by pushing the plug 81 distally (downwardly) to the bottom of the anchor device 80 so that it no longer presses the side walls outward. A pair of removal rods 100 are inserted into the guide holes 80e formed on the inside walls of the anchor device and squeezed together (direction of facing arrows). The plug in its loose position allows the squeezing of the removal rods to compress the side walls of the anchor device inwardly and disengage the blades 80d from the bone. The anchor device can then be removed by gripping the anchor device between the removal rods like chopsticks.

The anchor device of the present invention is uniquely configured to allow it to be installed quickly in a borehole formed in a bone in a manner such that the proximal end with or without an anchor plate can be positioned in alignment with the surface of the bone. The anchor can be used to attach bone to bone, soft tissue to bone, or implants to bone. Preferred uses include arthrodesis (fusion) of joints and fixation of fractures. It can also be used to repair or attach tendons or ligaments to bone, and to attach implants such as plates, rods, and prosthetic joints to bones in any suitable functioning area of the body.

Categories of surgery for use of the anchor include orthopedic surgery to repair fractures, repair soft tissue injuries, tumor surgery, joint replacement, and fusions. It can also be used in surgeries for spinal instrumentation, facet joint fixation, rotator cuff repair, other tendon repairs in large or small joints, anterior cruciate ligament reconstruction, total joint arthroplasty, and in just about any other anatomic site. Potential surgical procedures include open surgical procedures, microscopic procedures, and percutaneous endoscopic and arthroscopic procedures. The anchor can be readily adapted for use in other surgical fields including, but not limited to, neurosurgery, urologic surgery, general surgery, ENT surgery, and veterinary medicine.

It is understood that many modifications and variations may be devised given the above description of the principles of the invention. It is intended that all such modifications and variations be considered as within the spirit and scope of this invention, as defined in the following claims.

The invention claimed is:

1. An anchor device for installation in a borehole formed in a bone of a patient comprising:
   (a) an anchor body to be inserted in a borehole formed in a surface of a bone having expandable side walls in a tapered shape with a narrower proximal end thereof to face outwardly from the borehole and a wider distal end thereof to be inserted into the interior of the borehole, wherein said side walls have retention members formed on their external surfaces for inhibiting the anchor body from being retracted from the borehole when the side walls are expanded;
   (b) an expansion member positioned in an interior space defined within the side walls of the anchor body and movable from a disengaged position toward the distal end of the anchor body to an engaged position toward the proximal end of the anchor body, wherein when said expansion member is moved to the engaged position, it presses on the inside of the side walls of the anchor body to expand them outwardly in order to thereby engage the retention members with the borehole walls to inhibit retraction from the bone, and
   wherein said proximal end of the anchor body has a central aperture to allow insertion of a distal end of an elongated expansion tool into the interior space of the anchor body in order to grasp the expansion body in its disengaged position in the anchor body and pull the expansion member to the engaged position to thereby expand the side walls of the anchor body outwardly,
   wherein said expansion member is formed as a frusto-conically shaped plug, and
   wherein said anchor body has a pair of guide ribs provided along the inner surfaces of the side walls for guiding the movement of the expansion member from the disengaged to the engaged position, and said expansion member has a pair of slot recesses formed in its side walls for sliding along the guide ribs of the anchor body.

2. An anchor device according to claim 1, wherein said anchor body has slightly tapered walls that are sectioned by slits to form expandable side wall sections.

3. An anchor device according to claim 2, wherein said side walls are provided with an expansion joint between the expandable side wall sections and a solid ring of the side walls at the proximate end of the anchor body.

4. An anchor device according to claim 2, wherein said side walls are provided with a deformation wrinkle formed on the inner surfaces of the side walls between the expandable side wall sections and a solid ring of the side walls at the proximate end of the anchor body.

5. An anchor device according to claim 1, wherein said expansion member has a central aperture for insertion of an elongated scissors-type expansion tool having a pair of movable prongs at a distal end thereof, and tab recesses formed in an underside of the expansion member into which the prongs of the tool's distal end are engaged for pulling the expansion member to the engaged position.

6. An anchor device according to claim 1, wherein said guide ribs are formed as hollow tubes to allow insertion and squeezing together of the straight ends of a removal tool to dislodge the expansion member from the engaged position in the event removal of the anchor body is desired.

7. An anchor device according to claim 1, wherein said expansion member has a threaded bore for insertion of a threaded tip of an elongated expansion tool for pulling the expansion member to the engaged position.

8. An anchor device according to claim 1, wherein the inside surfaces of the side walls have containment ring sections formed at their distal ends for retaining the expansion member inside the anchor body.

9. An anchor device according to claim 1, wherein said retention members are formed as annular cutter blades that cut into the walls of the bone when the side walls of the anchor body are expanded.

10. An anchor device according to claim 1, wherein said anchor body is provided with an anchor plate at its proximal end to positively locate the anchor body in a desired position with its proximal end aligned with the bone surface.

11. A method for installing an anchor device in a borehole formed in a bone of a patient comprising:
    (a) inserting an anchor body in a borehole formed in a surface of a bone having expandable side walls in a tapered shape with a narrower proximal end thereof to face outwardly from the borehole and a wider distal end thereof inserted into the interior of the borehole, wherein said side walls have retention members formed on their external surfaces for inhibiting the anchor body from being refracted from the borehole when the side walls are expanded;
    (b) pulling an expansion member positioned in an interior space defined within the side walls of the anchor body from a disengaged position toward the distal end of the anchor body to an engaged position toward the proximal end of the anchor body wherein it presses on the inside of the side walls of the anchor body to expand them outwardly in order to thereby engage the retention members with the borehole walls to inhibit retraction from the bone,
    wherein pulling of the expansion member is obtained by providing the proximal end of the anchor body with a central aperture for inserting a distal end of an elongated expansion tool into the interior space of the anchor body in order to grasp the expansion body in its disengaged position and pull it to the engaged position to thereby expand the side walls of the anchor body outwardly, and
    wherein the anchor body is provided with a pair of guide ribs along the inner surfaces of the side walls for guiding the movement of the expansion member from the disengaged to the engaged position, and said expansion member has a pair of slot recesses formed in its side walls for sliding along the guide ribs of the anchor body.

12. A method for installing an anchor device according to claim 11, wherein the expansion member has a central aperture for insertion of an elongated scissors-type expansion tool having a pair of movable prongs at a distal end thereof, and tab recesses formed in an underside of the expansion member into which the prongs of the tool's distal end engage for pulling the expansion member to the engaged position.

13. A method for installing an anchor device according to claim 11, wherein the guide ribs are formed as hollow tubes to allow for dislodging the expansion member from the engaged position in the event removal of the anchor body is desired.

14. A method for installing an anchor device according to claim 13, wherein the removal tube consists of a pair of removal rods that are inserted into the hollow tubes of the guide ribs and squeezed together to dislodge the expansion member from the engaged position.

15. A method for installing an anchor device according to claim 11, wherein said expansion member has a threaded bore for insertion of a threaded tip of an elongated expansion tool for pulling the expansion member to the engaged position.

16. A method for installing an anchor device according to claim 11, further comprising the step of providing the anchor body with an anchor plate at its proximal end to positively locate the anchor body in a desired position with its proximal end aligned with and bonded to the bone surface.

17. A method for installing an anchor device according to claim 11 adapted for any of the group of surgical applications consisting of: orthopedic surgery to repair fractures, repair soft tissue injuries, tumor surgery, joint replacement, or fusions; surgery for spinal instrumentation; surgery for facet joint fixation; surgery for rotator cuff repair; surgery for tendon repairs in large or small joints; surgery for anterior cruciate ligament reconstruction; surgery for total joint arthroplasty; open surgical procedures; microscopic surgery procedures; percutaneous endoscopic or arthroscopic procedures; neurosurgery; urologic surgery; general surgery; ENT surgery; and veterinary medicine.

18. An anchor device according to claim 1, wherein said expansion member is provided with suture sleeves or anchor points for attachment of sutures thereto on an upper surface thereof facing outwardly from the borehole of the anchor device.

* * * * *